United States Patent [19]

Rosenberg et al.

[11] Patent Number: 4,958,046
[45] Date of Patent: Sep. 18, 1990

[54] HYDROXYPROPAFENONE GLYCERIDES

[75] Inventors: Joerg Rosenberg, Ludwigshafen; Juergen Heberger, Schifferstadt; Hans-Heinrich Gruenhagen, Ludwigshafen; Egon Brode, Frankenthal; Gerda von Philipsborn, Weinheim, all of Fed. Rep. of Germany

[73] Assignee: Knoll AG, Ludwigshafen, Fed. Rep. of Germany

[21] Appl. No.: 410,050

[22] Filed: Sep. 19, 1989

[30] Foreign Application Priority Data

Oct. 7, 1988 [DE] Fed. Rep. of Germany ........ 3834132

[51] Int. Cl.$^5$ ............................................ C07C 69/353
[52] U.S. Cl. ...................................... 560/142; 560/194
[58] Field of Search ................. 560/194, 142; 514/548

[56] References Cited

FOREIGN PATENT DOCUMENTS 0077529 7/1985 European Pat. Off. .

OTHER PUBLICATIONS

Acta Pharm. Suec. 23, (1986), 163–172.

*Primary Examiner*—Werren B. Lone
*Assistant Examiner*—Vera C. Clarke
*Attorney, Agent, or Firm*—Keil & Weinkauf

[57] ABSTRACT

Hydroxypropafenone glycerides of the formula I

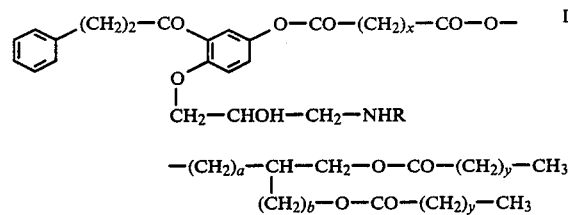

where
 R is n-propyl or 1,1-dimethylpropyl,
 x is 2 or 3,
 y is 12, 14, 16, 18 or 20, and
 a and b differ from one another and are 0 or 1, as well as the stereoisomers thereof and the preparation thereof are described. The compounds are suitable as active substances for antiarrhythmics.

3 Claims, No Drawings

HYDROXYPROPAFENONE GLYCERIDES

The present invention relates to novel hydroxypropafenone glycerides, and to the preparation and use thereof as active substances for antiarrhythmics.

Many active substances can, by reason of their hydrophilic nature, be absorbed to only a limited extent from the gastrointestinal tract by the cells in the intestinal wall. It may be possible, by making such active substances lipophilic by means of a glyceride residue which can easily be eliminated again under physiological conditions, to improve the absorption of hydrophilic active substances through membranes. The first-pass effect, which is pronounced with some hydrophilic active substances, may also be avoided, because the lipophilic derivatives of active substances are often absorbed via the lymph and thus avoid the first passage through the liver. The active substance can be made lipophilic, for example, using the process specified in EP-A 77,529, in which glyceride units are reacted with functional groups of the active substance by means of a dicarboxylic acid which acts as a bridge member. However, it has emerged that, for example, with the pindolol derivative prepared by the process in this publication it was not possible to obtain higher plasma pindolol concentrations with the lipophilic derivative, after oral administration of the same molar amount of active substance to dogs, than after administration of the active substance itself (Acta Pharm. Suec. 23 (1986), 163–172). Nor did the attempt to improve the absorption of the hydrophilic active substance heparin from the gastrointestinal tract by making it lipophilic with the above process succeed (T. Albig, Thesis, ETH Zurich, No. 7990 (1986)).

We have now found that the bioavailability of two active substances can be greatly improved by glyceride linkage.

The present invention relates to hydroxypropafenone glycerides of the formula I

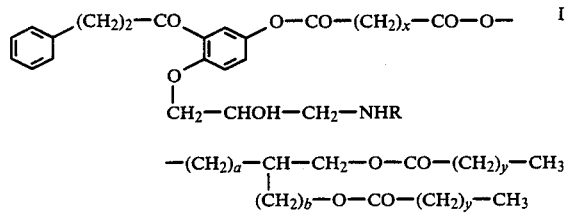

where
R is n-propyl or 1,1-dimethylpropyl,
x is 2 or 3 and
y is 12, 14, 16, 18 or 20 and
a and b differ from one another and are 0 or 1,
as well as the stereoisomers thereof.

The novel compounds have two asymmetric C atoms and can therefore exist in the form of stereoisomers.

The novel compounds can be prepared by reacting a compound of the formula II

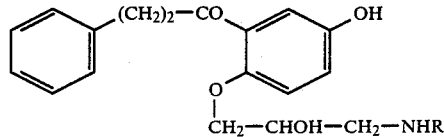

where R has the stated meaning, with a glyceride of the formula III

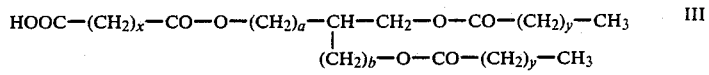

where x, y, a and b have the stated meanings.

For the reaction of compound II with III it is necessary initially to protect the NH group in II. This can take place with an amino protective group such as benzyl chloroformate. The protective group is introduced by methods known in peptide chemistry, e.g. in a two-phase mixture of diethyl ether and water.

The compound obtained in this way is then esterified with III, which in turn can take place by known methods, for example by converting III into the acid chloride with $SOCl_2$ and reacting the acid chloride, obtained in this way, with the compound II, which is protected on the amino group, in methylene chloride/pyridine at room temperature.

Surprisingly, the esterification takes place highly selectively at the phenolic hydroxyl group. The hydroxyl group on the aliphatic side-chain remains free during this and does not need to be provided with its own OH protective group.

After the esterification, the protective group is eliminated in a conventional manner, for example by hydrogenation with $Pd/H_2$ in ethyl methyl ketone under atmospheric pressure.

The starting materials of the formula II required for the reaction are known (German Patent No. 2,001,431, European Patent No. 75,207 (Example 71)).

The preparation of the stereoisomers starts from the optically active precursors.

The derivatization described above increases the bioavailability of compounds II, which is only about 5% after oral administration, by a factor of 4 to 5, i.e. the amount of active substance employed can be reduced by this factor.

This finding is surprising inasmuch as it is known that no improvement in the enteral availability is achieved by the stated process with pindolol and heparin. Even with propafenone no improvement in the enteral availability is achieved in this way.

Compounds I are suitable, like compounds II, for the therapy and prophylaxis of ventricular extrasystoles, ventricular tachycardias and tachyarrhythmias, supraventricular extrasystoles, tachycardias and tachyarrhythmias, as well as for the prophylaxis of ventricular fibrillation after electrical reversion.

The following examples illustrate the invention.

EXAMPLE 1

(a) Preparation of N-benzoyloxycarbonyl-5-hydroxypropafenone 321.7 g (0.9 mol) of 5-hydroxypropafenone (base) were suspended in a mixture of 1800 ml of diethyl ether and 1800 ml of water with 112.5 g of magnesium oxide.

Then, while cooling in ice and stirring vigorously, 307.1 g (0.9 mol) of a 50% strength benzyl chloroformate solution (in toluene) were added dropwise. After 2 h a further 15 ml of this solution were added. After 6 h 3000 ml of ethyl acetate were added, and concentrated hydrochloric acid was added dropwise until a clear solution was produced. The organic phase was separated off, filtered, washed with 1000 ml of hydrochloric acid (1 molar) and with water (1000 ml), dried over sodium sulfate and finally evaporated. 2000 ml of diisopropyl ether were added to the oily residue, and the mixture was left to crystallize with stirring. The crystals were filtered off with suction and then washed with a little diisopropyl ether and finally dried under reduced pressure.

Yield: 413 g (93%)

Melting point: 84°–86° C.

(b) Esterification of N-benzyloxycarbonyl-5-hydroxypropafenone with 1,2-dipalmitoylglycerol 3-(3-chloroformylpropionate)

235.6 g (0.48 mol) of N-benzyloxycarbonyl-5-hydroxypropafenone were dissolved in 2500 ml of dry dichloromethane. The mixture was cooled while stirring vigorously to an internal temperature of $-10°$ C. The following solutions were simultaneously added dropwise, from separate dropping funnels, to this mixture in such a way that at the end both dropping funnels were empty at the same time:

Solution 1:
  330 g (0.48 mol) of 1,2-dipalmitoylglycerol 3-(3-chloroformylpropionate) dissolved in 800 ml of dichloromethane;

Solution 2:
  48.4 g (0.48 mol) of triethylamine dissolved in 400 ml of dichloromethane.

After the addition was complete, the reaction solution was allowed to warm slowly to room temperature. The mixture was then extracted by shaking twice with 1200 ml of hydrochloric acid (1 molar) each time and finally with 1200 ml of water, and was dried over sodium sulfate and evaporated. 4000 ml of methanol were poured into the still warm oily residue, while stirring, the mixture was cooled in an ice bath while stirring, and the precipitate which had separated out was filtered off with suction at 8° C. and dried under reduced pressure.

Yield: 521 g (95%) Melting point: 34°–36° C.

(c) Preparation of the final product 342.3 g (0.3 mol) of the precursor obtained as in (b) were dissolved in 2000 ml of acetone, and 180 ml of hydrochloric acid (2 molar) were added. The apparatus was then flushed with nitrogen, 30 g of palladium/carbon (10%) were added, and the mixture was hydrogenated with gaseous hydrogen under atmospheric pressure at 40° C. The carbon dioxide which was produced was trapped with sodium hydroxide solution. After hydrogenation for 1 h, the carbon was filtered off with suction and briefly washed with acetone, and the filtrate was left to crystallize in an ice bath with stirring, and then the precipitate was filtered off with suction in a cold room, washed with a little cold acetone and finally dried under reduced pressure. The compound I, R=n-propyl, x=2, y=14, a=1, b=0, was obtained in this way.

Yield: 291 g (91%)

Melting point: 50°–51° C.

The following were prepared in a similar manner to Example 1:

2. Compound I, R=n-propyl, x=2, y=12, a=1, b=0,

Yield: 63%

Melting point: <30° C.

In the preparation of the final product the hydrogenation was complete after 2 h, and crystallization was carried out not with acetone but in 95:5 acetonitrile/methanol.

3. Compound I, R=n-propyl, x=2, y=14, a=0, b=1,

Yield: 78%

Melting point: 39°–41° C.

If optically active starting materials II or III are used in Examples 1 to 3, the compounds I are obtained in optically active form, and if II and III are employed as antipodes, the corresponding R,R, R,S, S,R and S,S enantiomers are obtained.

The compounds of the formula I listed in the Table which follows can be prepared similarly, in particular both as racemates and in the form of their antipodes or their R,R, R,S, S,R and S,S enantiomers.

TABLE

| R | x | y | a | b |
|---|---|---|---|---|
| n-Propyl | 2 | 12 | 1 | 0 |
| n-Propyl | 2 | 14 | 1 | 0 |
| n-Propyl | 2 | 16 | 1 | 0 |
| n-Propyl | 2 | 18 | 1 | 0 |
| n-Propyl | 2 | 20 | 1 | 0 |
| 1,1-Dimethylpropyl | 2 | 12 | 1 | 0 |
| 1,1-Dimethylpropyl | 2 | 14 | 1 | 0 |
| 1,1-Dimethylpropyl | 2 | 16 | 1 | 0 |
| 1,1-Dimethylpropyl | 2 | 18 | 1 | 0 |
| 1,1-Dimethylpropyl | 2 | 20 | 1 | 0 |
| n-Propyl | 3 | 12 | 1 | 0 |
| n-Propyl | 3 | 14 | 1 | 0 |
| n-Propyl | 3 | 16 | 1 | 0 |
| n-Propyl | 3 | 18 | 1 | 0 |
| n-Propyl | 3 | 20 | 1 | 0 |
| 1,1-Dimethylpropyl | 3 | 12 | 1 | 0 |
| 1,1-Dimethylpropyl | 3 | 14 | 1 | 0 |
| 1,1-Dimethylpropyl | 3 | 16 | 1 | 0 |
| 1,1-Dimethylpropyl | 3 | 18 | 1 | 0 |
| 1,1-Dimethylpropyl | 3 | 20 | 1 | 0 |
| n-Propyl | 2 | 12 | 0 | 1 |
| n-Propyl | 2 | 14 | 0 | 1 |
| n-Propyl | 2 | 16 | 0 | 1 |
| n-Propyl | 2 | 18 | 0 | 1 |
| n-Propyl | 2 | 20 | 0 | 1 |
| 1,1-Dimethylpropyl | 2 | 12 | 0 | 1 |
| 1,1-Dimethylpropyl | 2 | 14 | 0 | 1 |
| 1,1-Dimethylpropyl | 2 | 16 | 0 | 1 |
| 1,1-Dimethylpropyl | 2 | 18 | 0 | 1 |
| 1,1-Dimethylpropyl | 2 | 20 | 0 | 1 |
| n-Propyl | 3 | 12 | 0 | 1 |
| n-Propyl | 3 | 14 | 0 | 1 |
| n-Propyl | 3 | 16 | 0 | 1 |
| n-Propyl | 3 | 18 | 0 | 1 |
| n-Propyl | 3 | 20 | 0 | 1 |
| 1,1-Dimethylpropyl | 3 | 12 | 0 | 1 |
| 1,1-Dimethylpropyl | 3 | 14 | 0 | 1 |
| 1,1-Dimethylpropyl | 3 | 16 | 0 | 1 |
| 1,1-Dimethylpropyl | 3 | 18 | 0 | 1 |
| 1,1-Dimethylpropyl | 3 | 20 | 0 | 1 |

We claim:

1. A hydroxypropafenone glyceride of the formula I

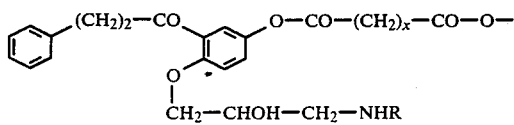
where
R is n-propyl or 1,1-dimethylpropyl,
x is 2 or 3,
y is 12, 14, 16, 18 or 20, and
a and b differ from one another and are 0 or 1, and the stereoisomers thereof.
2. A hydroxypropafenone glyceride as defined in claim 1, wherein R is n-propyl, x is 2 and y is 12, 14 or 16.
3. A hydroxypropafenone glyceride as defined in claim 1, wherein R is n-propyl, x is 2 and y is 14.
* * * * *